United States Patent
Prücher et al.

(10) Patent No.: US 6,548,516 B1
(45) Date of Patent: Apr. 15, 2003

(54) 1-(3-HETEROARYLPROPYL- OR -PROP-2-ENYL)-4-BENZYLPIPERIDINES USED AS NMDA RECEPTOR ANTAGONISTS

(75) Inventors: Helmut Prücher, Heppenheim (DE); Joachim Leibrock, Pfungstadt (DE); Andrew Barber, Weiterstadt (DE); Gerd Bartoszyk, Weiterstadt (DE)

(73) Assignee: Merck Patent GmbH, Darmstadt (DE)

(*) Notice: Subject to any disclaimer, the term of this patent is extended or adjusted under 35 U.S.C. 154(b) by 0 days.

(21) Appl. No.: 09/646,185
(22) PCT Filed: Mar. 11, 1999
(86) PCT No.: PCT/EP99/01573
§ 371 (c)(1), (2), (4) Date: Sep. 14, 2000
(87) PCT Pub. No.: WO99/48891
PCT Pub. Date: Sep. 30, 1999

(30) Foreign Application Priority Data

Mar. 20, 1998 (DE) ......... 198 12 331

(51) Int. Cl.$^7$ ............ A61K 31/445; C07D 401/00; C07D 223/10
(52) U.S. Cl. ............ 514/321; 546/198; 546/187; 546/201; 540/485; 514/322; 514/323
(58) Field of Search ............ 546/198, 187, 546/201; 514/321, 322, 323; 540/485

(56) References Cited

U.S. PATENT DOCUMENTS 5,534,511 A * 7/1996 Mouithys-Mickalad et al.
5,688,811 A * 11/1997 Mouithys-Mickalad et al. . 514/321

FOREIGN PATENT DOCUMENTS

| DE | 196 43 790 | | 5/1998 |
| EP | 0 648 744 | | 4/1995 |
| EP | 0 709 384 | | 5/1996 |
| FR | 2 477 542 | | 9/1981 |
| FR | 2477542 | * | 9/1981 |
| WO | WO 9723216 | * | 9/1981 |
| WO | 96 02250 | | 2/1996 |
| WO | 97 23216 | | 7/1997 |

* cited by examiner

*Primary Examiner*—Alan L. Rotman
*Assistant Examiner*—Binta M. Robinson
(74) *Attorney, Agent, or Firm*—Millen, White, Zelano & Branigan, P.C.

(57) ABSTRACT

Piperidine derivatives of the formula I

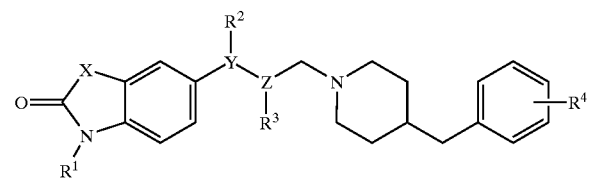

and their physiologically acceptable salts
in which X, Y, Z, R$^1$, R$^2$, R$^3$ and R$^4$ are as defined in claim 1
can be as excitatory amino acid antagonists for combating neurodegenerative disorders including cerebrovascular diseases, epilepsy, schizophrenia, Alzheimer's disease, Parkinson's disease and Huntington's disease, cerebral ischaemias, infarcts and psychosis.

8 Claims, No Drawings

1-(3-HETEROARYLPROPYL- OR -PROP-2-ENYL)-4-BENZYLPIPERIDINES USED AS NMDA RECEPTOR ANTAGONISTS

The invention relates to piperidine derivatives of the formula I

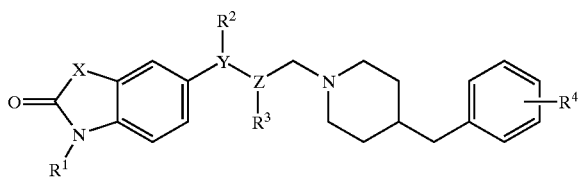

in which
X is O, $NR^1$, S or $(CH_2)_n$,
Y is CH,
Z is CH,
where Y and Z together can also be C=C,
$R^1$, $R^2$ and R3 each independently of one another are H or A,
$R^4$ is H, Hal, A or OA,
A is alkyl having 1–6 carbon atoms,
Hal is F, Cl, Br or I and
n is 1, 2 or 3,
and their physiologically acceptable salts.

Benzylpiperidine derivatives having a high affinity for binding sites of amino acid receptors are known, for example, from EP 0 709 384 A1.

The object of the invention was to discover novel compounds having useful properties, especially compounds which can be used for preparing medicaments.

It has been found that the compounds of the formula I and their salts are not only well tolerated but also have very useful pharmacological properties. In particular, they have a very high affinity for binding sites of amino acid receptors, especially for the ifenprodil binding site on the NMDA receptor (NMDA=N-methyl-D-aspartate), which modulates the polyamine binding site allosterically.

The binding test for [$^3$H]-ifenprodil can be conducted by the method of Schoemaker et al., Eur. J. Pharmacol. 176, 249–250 (1990). The compounds are suitable for treating neurodegenerative disorders, including cerebrovascular diseases. The novel compounds can also be used as an analgesic or anxiolytic and in the treatment of epilepsy, schizophrenia, Alzheimer's disease, Parkinson's disease and Huntington's disease, cerebral ischaemias or infarcts. Furthermore, they are suitable for treating psychoses caused by excessively high amino acid levels.

The [$^3$H]-CGP-39653 binding test for the glutamate binding site of the NMDA receptor can be conducted, for example, by the method of M. A. Stills et al., described in Eur. J. Pharmacol. 192, 19–24 (1991). The test for the glycine binding site of the NMDA receptor can be conducted by the method of M. B. Baron et al., described in Eur. J. Pharmacol. 206, 149–154 (1991).

The activity against Parkinson's disease, i.e. the potentiation of the L-DOPA-induced contralateral pivoting in hemiparkinsonian rats, can be detected by the method of U. Ungerstedt and G. W. Arbuthnott, Brain Res. 24, 485 (1970).

The compound is particularly suitable for treatment or prophylaxis of strokes and for protection against and treatment of cerebral oedemas and states of undersupply of the central nervous system, especially hypoxia or anoxia.

The activities referred to can, moreover, be detected or checked by methods such as those described in the following literature references:

J. W. McDonald, F. S. Silverstein and M. V. Johnston, Eur. J. Pharmacol. 140, 359 (1987); R. Gill, A. C. Foster and G. N. Woodruff, J. Neurosci. 7, 3343 (1987); J. B. Bederson et al., Stroke, 17, 472–476 (1986); S. Brint et al., J. Cereb. Blood Flow Metab. 8, 474–485 (1988).

The literature references listed below disclose a variety of antagonists which are able to block different binding sites of the NMDA receptor:
W. Danysz, C. G. Parsons, I. Bresink and G. Quack, Drug, News & Perspective 8, 261 (1995), K. R. Gee, Exp. Opin. Invest. Drugs 3, 1021 (1994) and J. J. Kulagowski and L. L. Iversen, J. Med. Chem. 37, 4053 (1994).

Ifenprodil and eliprodil, of the formulae IIIa and IV respectively, are able to block the NMDA receptor by interacting with the modulatory polyamine binding site (C. J. Carter, K. G. Lloyd, B. Zivkovic and B. Scatton, J. Pharmacol. Exp. Ther. 253, 475 (1990)).

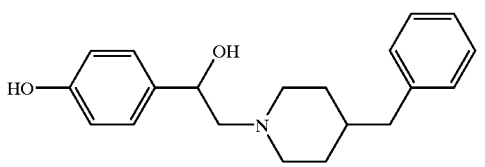

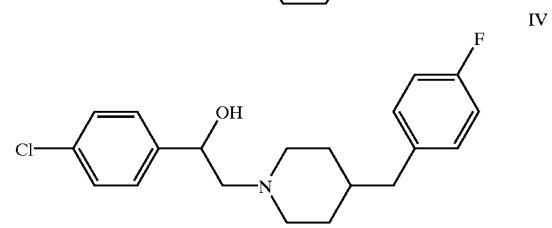

Since ifenprodil and eliprodil interact with the polyamine binding site on the NMDA receptor, the antagonistic activity of the compounds of the invention can be determined using a spermine-stimulated [$^3$H]-MK-801 (dizocilpine) binding test.

In the presence of saturation concentrations of glycine and NMDA, spermine is still able to increase the binding of MK-801, which is inhibited by ifenprodil, eliprodil and, very effectively, by the compounds of the invention.

In addition, the compounds of the invention can be tested in a [$^3$H]-GABA (γ-aminobutyric) release test, in analogy to J. Dreijer, T. Honoré and A. Schousboe, J. Neurosci. 7, 2910 (1987), which is an in vitro model describing the antagonistic function in the cell.

The invention provides, accordingly, the compounds of the formula I according to claim 1 and/or their physiologically acceptable salts as antagonists to receptors of excitatory amino acids, such as glutamic acid or its salts.

The invention provides, in particular, the compounds of the formula I according to claim 1 and/or their acceptable salts as excitatory amino acid antagonists for combating neurodegenerative disorders including cerebrovascular diseases, epilepsy, schizophrenia, Alzheimer's disease, Parkinson's disease and Huntington's disease, cerebral ischaemias, infarcts and psychoses.

The invention also provides for the use of the compounds of the formula I according to claim 1 and/or their physiologically acceptable salts for preparing a medicament for combating neurodegenerative disorders including cerebrovascular diseases, epilepsy, schizophrenia, Alzheimer's disease, Parkinson's disease and Huntington's disease, cerebral ischaemias, infarcts and psychoses.

The compounds of the formula I can be employed as an active principle of medicaments in human and veterinary medicine.

The invention additionally provides a process for preparing the compounds of the formula I according to claim 1 and their physiologically acceptable salts, characterized in that
a) a compound of the formula II

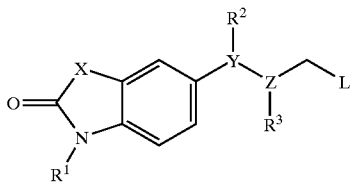

in which
L is Cl, Br, I, OH or a reactively esterified OH group, and X, Y, Z, $R^1$, $R^2$ and $R^3$ are as defined in claim 1
is reacted with a compound of the formula III

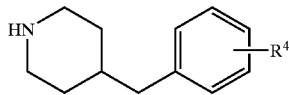

in which $R^4$ is as defined in claim 1, or
b) a compound of the formula I in which X, $R^1$, $R^2$, $R^3$ and $R^4$ are as defined in claim 1, and Y and Z together are C=C is hydrogenated, or
c) water or L'H is eliminated from a compound of the formula I in which X, $R^1$, $R^3$ and $R^4$ are as defined in claim 1,
Y is CH,
Z is CH and
$R^2$ is OH or L', in which L' is Cl, Br, I, or a reactively esterified OH group, and/or
d) a compound of the formula I is converted by treatment with an acid into one of its salts.

Accordingly, the invention provides in particular those compounds of the formula I in which at least one of the stated radicals has one of the preferred definitions indicated above. Some preferred groups of compounds can be expressed by the following subformulae Ia to Ic, which correspond to the formula I and in which those radicals not identified in any more detail are as defined for the formula I, but in which
in Ia
  $R^1$ is H;
in Ib
  $R^1$ is H and
  X is O,$NR^1$ or S;
in Ic
  $R^1$ is H,
  X O, $NR^1$ or S,
  $R^2$ is H,
  $R^3$ is H or A and
  $R^4$ is Hal.

Alkyl is preferably unbranched and has 1, 2, 3, 4, 5, 6, 7, 8, 9 or 10 carbon atoms, preferably 1, 2, 3, 4 or 5 carbon atoms, and is preferably methyl, ethyl, trifluoromethyl, pentafluoroethyl or propyl, and also preferably isopropyl, butyl, isobutyl, sec-butyl or tert-butyl, but also n-pentyl, neopentyl, isopentyl or hexyl.

The compounds of the formula I and also the starting materials for their preparation are otherwise prepared by methods known per se, as are described in the literature (e.g. in the standard works such as Houben-Weyl, Methoden der organischen Chemie, Georg-Thieme-Verlag, Stuttgart) under reaction conditions which are known and suitable for the stated reactions. In this context it is also possible to make use of variants which are known per se but are not mentioned in any greater detail here.

If desired, the starting materials can also be formed in situ such that they are not isolated from the reaction mixture but instead are immediately reacted further to give the compound of the formula I.

The compounds of the formula I can preferably be obtained by reacting compounds of the formula II with compounds of the formula III.

The starting compounds of the formula II are generally novel. However, they can be prepared by methods which are known per se.

In the compounds of the formula II, L is preferably Cl, Br, I, OH or a reactively modified OH group such as alkylsulfonyloxy having 1–6 carbon atoms (preferably methylsulfonyloxy) or arylsulfonyloxy having 6–10 carbon atoms (preferably phenyl- or p-tolylsulfonyloxy).

The reaction of the compounds of the formula II with compounds of the formula III generally takes place in an inert solvent, in the presence of an acid-binding agent, preferably an organic base such as triethylamine, dimethylaniline, pyridine or quinoline.

It may also be advantageous to add a hydroxide, carbonate or bicarbonate of an alkali metal or alkaline earth metal, or another salt of a weak acid of the alkali metals or alkaline earth metals, preferably of potassium, sodium, calcium or caesium.

Depending on the conditions employed, the reaction time lies between several minutes and 14 days, the reaction temperature between about −30° and 140°, normally between −10° and 90° and, in particular, between about 0° and about 70°.

Examples of suitable inert solvents are hydrocarbons such as hexane, petroleum ether, benzene, toluene or xylene; chlorinated hydrocarbons such as trichloroethylene, 1,2-dichloroethane, carbon tetra-chloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, water, or mixtures of the stated solvents.

Compounds of the formula I in which Y and Z are each CH can also be prepared, preferably, by hydrogenation from the compounds of the formula I in which Y and Z together are C=C.

For this purpose it is preferred to employ catalytic hydrogenation with, for example, palladium on active carbon and hydrogen.

Examples of suitable catalysts for the catalytic hydrogenation are noble metal catalysts and nickel and cobalt catalysts. The noble metal catalysts can be on supports (e.g. platinum or palladium on carbon, palladium on calcium carbonate or strontium carbonate), can be oxide catalysts (e.g. platinum oxide), or can be finely divided metal catalysts. Nickel catalysts and cobalt catalysts are judiciously employed as Raney metals, nickel also on kieselguhr or pumice as support. The hydrogenation can be conducted at room temperature and atmospheric pressure or else at elevated temperature and/or increased pressure. It is preferred to operate at pressures between 1 and 100 bar and at temperatures between −80 and +150° C., primarily between room temperature and 100° C. The reaction is judiciously conducted in the acidic, neutral or basic range and in the presence of a solvent, such as water, methanol, ethanol, isopropanol, n-butanol, ethyl acetate, dioxane, acetic acid or THF; mixtures of these solvents can also be employed.

Compounds of the formula I in which Y and Z together are C=C can preferably be obtained from compounds of the formula I in which X, $R^1$, $R^3$ and $R^4$ are as defined in claim 1, Y is CH, Z is CH and $R^2$ is OH or L', in which L' is Cl, Br, I, OH or a reactively esterified OH group, by eliminating water or L'H from these compounds.

Elimination is preferably conducted with aqueous acids, especially aqueous mineral acids.

L'is, for example, preferably Cl, Br, I or a reactively modified OH group such as alkylsulfonyloxy having 1–6 carbon atoms (preferably methylsulfonyloxy) or arylsulfonyloxy having 6–10 carbon atoms (preferably phenyl- or p-tolylsulfonyloxy).

The compounds in which $R^2$ is OH or L' can be obtained by reduction, for example, from compounds in which Y and $R^2$ together form a carbonyl group.

The reduction can take place as indicated by catalytic hydrogenation, or with complex metal hydrides.

Examples of complex metal hydrides which can be employed are $NaBH_4$, diisobutylaluminium hydride or $NaAl(OCH_2CH_2OCH_3)_2H_2$ and also diborane, with the addition if desired of catalysts such as $BF_3$, $AlCl_3$ or LiBr. Solvents suitable for this purpose are, in particular, ethers, such as diethyl ether, di-n-butyl ether, THF, dioxane, diglyme or 1,2-dimethoxyethane, and hydrocarbons, such as benzene. For a reduction with $NaBH_4$, those solvents which are primarily suitable are alcohols such as methanol or ethanol, and also water, and aqueous alcohols. In accordance with these methods, reduction is carried out preferably at temperatures between −80 and +150° C., in particular between 0 and about 100° C.

The conversion of an OH group into an OL' group is effected by known and customary methods.

A base of the formula I can be converted into the associated acid addition salt using an acid by means, for example, of reacting equivalent amounts of the base and the acid in an inert solvent such as ethanol, followed by evaporative concentration. Particularly suitable acids for this reaction are those which form physiologically acceptable salts. For instance, it is possible to use inorganic acids, examples being sulfuric acid, nitric acid, hydrohalic acids such as hydrochloric or hydrobromic acid, phosphoric acids such as ortho-phosphoric acid, sulfamic acid, and also organic acids, especially aliphatic, alicyclic, araliphatic, aromatic or heterocyclic mono- or polybasic carboxylic, sulfonic or sulfuric acids, examples being formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids, and laurylsulfuric acid. Salts with physiologically unacceptable acids, such as picrates, can be used to isolate and/or purify the compounds of the formula I.

The invention additionally provides for the use of the compounds of the formula I and/or their physiologically acceptable salts for manufacturing pharmaceutical preparations, especially by a non-chemical route. In this case they can be brought into a suitable dosage form together with at least one solid, liquid and/or semiliquid excipient or auxiliary and, if appropriate, in combination with one or more further active substances.

The invention additionally provides pharmaceutical preparations comprising an effective amount of at least one of the compounds of the formula I and/or one of their physiologically acceptable salts.

These preparations can be used as medicaments in human or veterinary medicine. Suitable excipients are organic or inorganic substances which are suitable for enteral (e.g. oral) or parenteral administration, topical application, or administration in the form of an inhalation spray and which do not react with the novel compounds, examples being water, vegetable oils, benzyl alcohols, alkylene glycols, polyethylene glycols, glyceryl triacetate, gelatin, carbohydrates such as lactose or starch, magnesium stearate, talc and vaseline. Plain tablets, pills, coated tablets, capsules, powders, granules, syrups, juices or drops are used in particular for oral administration, suppositories for rectal administration, solutions, preferably oily or aqueous solutions, and also suspensions, emulsions or implants, for parenteral administration, and ointments, creams or fine powders for topical application. The novel compounds can also be lyophilised and the resultant lyophilisates used, for example, to manufacture preparations for injection. The preparations indicated can be sterilized and/or may include auxiliaries such as lubricants, preservatives, stabilizers and/or wetting agents, emulsifiers, salts for influencing the osmotic pressure, buffer substances, colorants, flavourings and/or a plurality of further active ingredients, such as one or more vitamins.

For administration as an inhalation spray it is possible to use sprays which comprise the active substance either dissolved or suspended in a propellant or mixture of propellants (e.g. $CO_2$ or chloro-fluorocarbons). In this case, the active substances are judiciously used in micronized form with the possible presence of one or more additional physiologically compatible solvents, such as ethanol. Inhalation solutions can be administered using customary inhalers.

The compounds of the formula I and their physiologically acceptable salts can be used as excitatory amino acid antagonists in the combating of diseases, especially for combating neurodegenerative disorders including cerebrovascular diseases, epilepsy, schizophrenia, Alzheimer's disease, Parkinson's disease and Huntington's disease, cerebral ischaemias, infarcts and psychoses.

In these treatments, the compounds of the invention can generally be administered in analogy to other known compounds having a similar profile of action, such as ifenprodil, preferably in doses of between about 0.05 and 500 mg, in particular between 0.5 and 100 mg per dose unit. The daily dose is preferably between about 0.01 and 2 mg/kg of body weight. The specific dose for each patient, however, will depend on a wide variety of factors: for example, on the efficacy of the specific compound employed, on the age, body weight, general state of health, sex, diet, time and route of administration, rate of excretion, medicament combination and severity of the respective disorder to which the therapy is applied. Parenteral administration is preferred.

Above and below, all temperatures are indicated in °C. In the examples below, "customary workup" means: water is added if necessary, the mixture is adjusted to a pH of between 2 and 10 if necessary, depending on the constitution of the end product, the mixture is extracted with ethyl acetate or dichloromethane, the organic phase is separated off, dried over sodium sulfate and concentrated by evaporation, and the residue is purified by chromatography on silica gel and/or by crystallization.

EXAMPLE 1

A suspension of 5.5 g of 6-(3-chloropropyl)-3H-benzoxazol-2-one in 50 ml of ethanol is admixed with 5.7 g of 4-(4-fluorobenzyl)piperidine hydrochloride and 7.2 ml of triethylamine. The mixture is stirred under reflux for one hour and subjected to customary workup to give 8.5 g of 6-{3-[4-(4-fluorobenzyl)piperid-1-yl]propyl}-3H-benzoxazol-2-one, m.p. 105–107°.

EXAMPLE 2

A solution of 6.7 g of 6-{3-[4-(4-fluorobenzyl)piperid-1-yl]-1-hydroxypropyl}-3H-benzoxazol-2-one [obtainable by hydrogenation of 6-{3-[4-(4-fluorobenzyl)piperid-1-yl]-1-oxopropyl}-3H-benzoxazol-2-one, which can be obtained by reacting 4-(4-fluorobenzyl)piperidine and 6-(3-chloropropionyl)-3H-benzoxazol-2-one] in 70 ml of dioxane is heated under reflux with 7 ml of concentrated HCl for 1.5 h. The mixture is cooled and 8.5 g of $NaHCO_3$ and 70 ml of water are added. 30 ml of dichloromethane are added and the mixture is stirred for 30 minutes. The precipitate is separated off, washed with acetone and ether and dried to give 5.7 g of 6-{3-[4-(4-fluorobenzyl)piperid-1-yl]propenyl}-3H-benzoxazol-2-one ("A"), m.p. 202–203.5°; hydrochloride: m.p. 220–223°.

The following compounds are obtained analogously:

6-{3-[4-(4-fluorobenzyl)piperid-1-yl]-2-methylpropenyl}-3H-benzoxazol-2-one, m.p. 156–160°, hydrochloride: 230–235°;
6-{3-[4-(4-fluorobenzyl)piperid-1-yl]propenyl}-3H-benzothiazol-2-one, hydrochloride×$H_2O$, m.p. 95–99° (decomposition);
5-{3-[4-(4-fluorobenzyl)piperid-1-yl]propenyl}-1,3-dihydrobenzimidazol-2-one, m.p. 218–220°; hydrochloride: 243–245°.
5-{3-[4-(4-fluorobenzyl)piperid-1-yl]propenyl}-1,3-dihydroindol-2-one;
6-{3-[4-(4-fluorobenzyl)piperid-1-yl]propenyl}-3,4-dihydro-1H-quinolin-2-one.

EXAMPLE 3

A solution of 2.56 g of "A" in 100 ml of methanol and 100 ml of THF is hydrogenated at room temperature with addition of 1.2 g of Pd/C. The catalyst is separated off and the mixture is subjected to customary work up to give 1.31 g of 6-{3-[4-(4-fluorobenzyl)piperid-1-yl]propyl}-3H-benzoxazol-2-one, m.p. 105–107°.

The following compounds are obtained analogously, by hydrogenation:

from 6-{3-[4-(4-fluorobenzyl)piperid-1-yl]-2-methylpropenyl}-3H-benzoxazol-2-one
6-{3-[4-(4-fluorobenzyl)piperid-1-yl]2-methylpropyl}-3H-benzoxazol-2-one;
from 6-{3-[4-(4-fluorobenzyl)piperid-1-yl]propenyl}-3H-benzothiazol-2-one:
6-{3-[4-(4-fluorobenzyl)piperid-1-yl]propyl}-3H-benzothiazol-2-one;
from 5-{3-[4-(4-fluorobenzyl)piperid-1-yl]propenyl}-1,3-dihydrobenzimidazol-2-one:
5-{3-[4-(4-fluorobenzyl)piperid-1-yl]propyl}-1,3-dihydrobenzimidazol-2-one;
from 5-{3-[4-(4-fluorobenzyl)piperid-1-yl]propenyl}-1,3-dihydroindol-2-one:
5-{3-[4-(4-fluorobenzyl)piperid-1-yl]propyl}-1,3-dihydroindol-2-one;
from 6-{3-[4-(4-fluorobenzyl)piperid-1-yl]propenyl}-3,4-dihydro-1H-quinolin-2-one:
6-{3-[4-(4-fluorobenzyl)piperid-1-yl]propyl}-3,4-dihydro-1H-quinolin-2-one.

The following examples relate to pharmaceutical preparations:

EXAMPLE A

Injection Vials

A solution of 100 g of the active substance of the formula I and 5 g of disodium hydrogen phosphate in 3 l of double-distilled water is adjusted to a pH of 6.5 with 2 N hydrochloric acid, sterile-filtered, transferred to injection vials, lyophilized under sterile conditions and sterile-sealed. Each vial contains 5 mg of active substance.

EXAMPLE B

Suppositories

A mixture of 20 g of the active substance of the formula I is melted together with 100 g of soya lecithin and 1400 g of cocoa butter and the mixture is poured into moulds and left to cool. Each Suppository contains 20 mg of active substance.

EXAMPLE C

Solution

A solution is prepared from 1 g of the active substance of the formula I, and 9.38 g of $NaH_2PO_4.2H_2O$, 28.48 g of $Na_2HPO_4.12H_2O$ and 0.1 g of benzalkonium chloride in 940 ml of double-distilled water. The pH is adjusted to 6.8, and the solution is made up to 1 l and sterilized by irradiation. This solution can be used in the form of eyedrops.

EXAMPLE D

Ointment 500 mg of the active substance of the formula I are mixed with 99.5 g of vaseline under aseptic conditions.

EXAMPLE E

Tablets

A mixture of 1 kg of active substance of the formula I, 4 kg of lactose, 1.2 kg of potato starch, 0.2 kg of talc and 0.1 kg of magnesium stearate is compressed into tablets in a customary manner such that each tablet contains 10 mg of active substance.

EXAMPLE F

Coated tablets

Tablets are pressed as in Example E and are then coated in a customary manner with a coating of sucrose, potato starch, talc, tragacanth and colorant.

EXAMPLE G

Capsules 2 kg of active substance of the formula I are filled into hard gelatine capsules in a customary manner such that each capsule contains 20 mg of active substance.

EXAMPLE H

Ampoules

A solution of 1 kg of active substance of the formula I in 60 l of double-distilled water is sterile-filtered, filled into ampoules and lyophilized under sterile conditions and the ampoules are sterile-sealed. Each ampoule contains 10 mg of active substance.

EXAMPLE I

Inhalation spray 14 g of active substance of the formula I are dissolved in 10 l of isotonic NaCl solution and the solution is filled into customary commercial spray containers having a pump mechanism. The solution can be sprayed into the mouth or nose. One burst of spray (about 0.1 ml) corresponds to a dose of about 0.14 mg.

What is claimed is:

1. A compound which is a) 6-{3-[4-(4-fluorobenzyl)piperid-1-yl]propenyl}-3H-benzoxazol-2-one;
b) 6-{3-[4-(4-fluorobenzyl)piperid-1-yl]propyl}-3H-benzoxazol-2-one;
c) 6-{3-[4-(4-fluorobenzyl)piperid-1-yl]propenyl}-3H-benzothiazol-2-one;
d) 5-{3-[4-(4-fluorobenzyl)piperid-1-yl]propenyl}-1,3-benzimidazol-2-one or
e) 5-{3-[4-(4-fluorobenzyl)piperid-1-yl]propenyl}-1,3-dihydroindol-2-one.

2. A compound according to claim 1 which is a) 6-{3-[4-(4-fluorobenzyl)piperid-1-yl}propenyl}-3H-benzoxazol-2-one
b) 6-{3-[4-(4-fluorobenzyl)piperid-1-yl}propyl}-3H-benzoxazol-2-one; or
c) 6-{3-[4-(4-fluorobenzyl)piperid-1-yl}propenyl}-3H-benzothiazol-2-one.

3. A process for preparing 6-{3-[4-(4-fluorobenzyl)piperid-1-yl]propenyl}-3H-benzoxazol-2-one, 6-{3-[4-(4-fluorobenzyl)piperid-1yl]propyl}-3H-benzoxazol-2-one, 6-{3-[4-(4-fluorobenzyl)piperid-1-yl]propenyl}-3H-benzothiazol-2-one, 5-{3-[4-(4-fluorobenzyl)piperid-1-yl]prophenyl}-1,3-benzimidazol-2-one or 5-{3-[4-(4-fluorobenzyl)piperid-1-yl]propenyl}-1,3-dihydroindol-2-one, or a salt thereof, comprising a) reacting a compound of the formula II

II in which
L is Cl, Br, I, OH or a reactively esterified OH group, and
$R^1$, $R^2$ and $R^3$ are H
X is O, N, CH, or S,
Y is CH,
Z is CH, or
Y and Z together are alternatively C=C
with a compound of the formula III

III in which $R^4$ is F, and is in the 4 position. or b) hydrogenating a compound of formula I

I in which
X is O, N, CH, or S,
Y and Z together are C=C
$R^1$, $R^2$ and $R^3$ are H,
$R^4$ is F, and is in the 4 position, or c) eliminating water or L'H from a compound of formula in which
$R^1$ is OH or L', in which L' is Cl, Br, I, or a reactively esterified OH group,
$R^2$ and $R^3$ are H,
$R^4$ is F, and is in the 4 position,
X is O, N, CH, or S,
Y is CH, and
Z is CH, and/or d) converting 6-{3-[4-(4-fluorobenzyl)piperid-1-yl]propenyl}-3H-benzoxazol-2-one, 6-{3-[4-(4-fluorobenzyl)piperid-1-yl]propyl}-3H-benzoxazol-2-one, 6-{3-[4-(4-fluorobenzyl)piperid-1-yl]propenyl}-3H-benzothiazol-2-one, 5-{3-[4-(4-fluorobenzyl)piperid-1-yl]propenyl}-1,3-benzimidazol-2-one, or 5-{3-[4-(4-fluorobenzyl)piperid-1-yl]propenyl}-1,3-dihydroindol-2-one, by treatment with an acid into one of its salts.

4. A process for preparing a pharmaceutical composition comprising bringing a compound according to claim 1 and/or one of its physiologically acceptable salts into a suitable dosage form together with at least one solid, liquid or semiliquid excipient or auxiliary.

5. A pharmaceutical composition comprising an effective amount of at least one compound of claim 1 and/or a physiologically acceptable salt thereof.

6. A process for treating or prophylaxis of strokes or cerebral oedemas comprising administering to a host in need thereof an effective amount of a compound according to claim 1, or a physiologically acceptable salt thereof.

7. A process for treating or protecting against cerebral oedemas comprising administering to a host in need thereof an effective amount of a compound according to claim 1, or a physiologically acceptable salt thereof.

8. A process for treating or protecting against hypoxia comprising administering to a host in need thereof an effective amount of a compound according to claim 1, or a physiologically acceptable salt thereof.

* * * * *

UNITED STATES PATENT AND TRADEMARK OFFICE
CERTIFICATE OF CORRECTION

PATENT NO.   : 6,548,516 B1
DATED        : April 15, 2003
INVENTOR(S)  : Helmut Pruecher It is certified that error appears in the above-identified patent and that said Letters Patent is hereby corrected as shown below:

Column 9,
Line 30, reads "prophenyl" should read -- propenyl --
Line 49, reads "CH" should read -- $CH_2$ --
Line 61, reads "position." should read -- position, --

Column 10,
Lines 13 and 32, reads "CH" should read -- $CH_2$ --
Line 28, reads "$R^1$" should read -- $R^2$ --
Line 30, reads "$R^2$" should read -- $R^1$ --

Signed and Sealed this

Eleventh Day of January, 2005

JON W. DUDAS
*Director of the United States Patent and Trademark Office*